United States Patent [19]

Banko

[11] 4,210,146
[45] Jul. 1, 1980

[54] SURGICAL INSTRUMENT WITH FLEXIBLE BLADE

[76] Inventor: Anton Banko, 1496 Mayflower Ave., Bronx, N.Y. 10461

[21] Appl. No.: 911,677

[22] Filed: Jun. 1, 1978

[51] Int. Cl.² ............................................. A61B 17/32
[52] U.S. Cl. ...................................... 128/305; 30/241
[58] Field of Search ........ 128/305, 2 B, 276, 751–755; 30/29.5, 241, 242, 243

[56] References Cited

U.S. PATENT DOCUMENTS

| | | | |
|---|---|---|---|
| 1,973,631 | 9/1934 | Johnson | 30/29.5 |
| 3,596,525 | 8/1971 | Niesz | 30/392 X |
| 3,815,604 | 6/1974 | O'Malley et al. | 128/305 |
| 3,884,238 | 5/1975 | O'Malley et al. | 128/305 |

FOREIGN PATENT DOCUMENTS 1922584 12/1969 Fed. Rep. of Germany ........... 128/305

*Primary Examiner*—Robert W. Michell
*Assistant Examiner*—Michael H. Thaler
*Attorney, Agent, or Firm*—Darby & Darby

[57] ABSTRACT

A surgical instrument with a bendable blade which moves with respect to an opening in the instrument tip to make a shearing action to cut tissue which enters the opening.

9 Claims, 4 Drawing Figures

U.S. Patent  Jul. 1, 1980  4,210,146
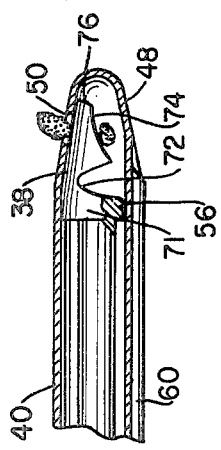
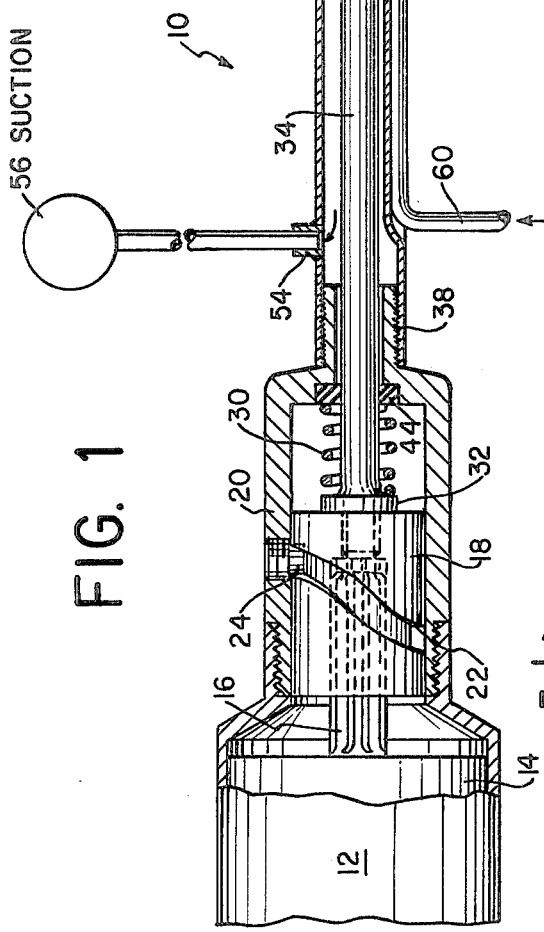
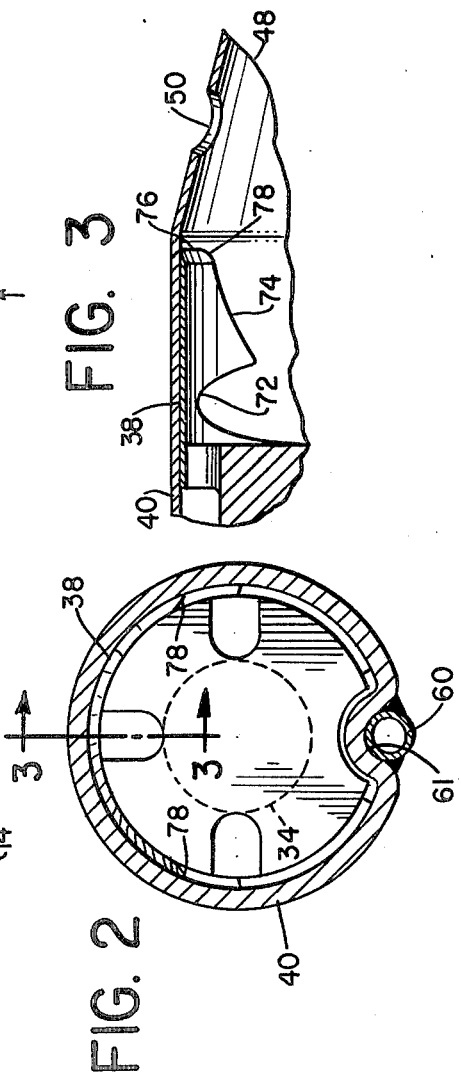
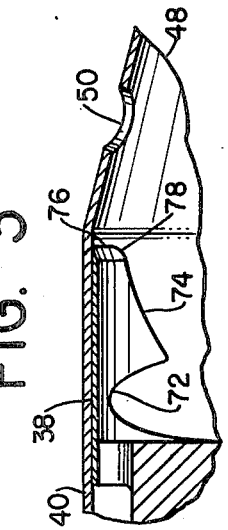

SURGICAL INSTRUMENT WITH FLEXIBLE BLADE

Various types of instruments have been developed for cutting tissue. Typical of such instruments are those shown in my U.S. Pat. Nos. 3,732,858 and 3,844,372, among others, which are particularly adapted for cutting tissue and other objects in the eye and other confined operating fields either by a rotating and/or reciprocating motion.

In each of the cutters of the foregoing patents, the cutter tool, or blade, is of a fixed configuration, that is, it does not change its physical configuration. In certain applications, a different type of cutter is required in which a shearing action is used in conjunction with a reciprocating motion of a cutter blade.

In accordance with the subject invention, a novel surgical instrument is provided which has a tubular member in which a cutter blade of spring-type material is located. The tubular member has tapered end portion in which is located an opening into which the tissue or other object which is to be cut is drawn, preferably by suction applied through the interior of the tube. A blade is provided which is connected to a mechanism for a reciprocating the blade with respect to the opening. Shearing, or cutting, of the tissue occurs as the blade moves past the opening. The blade is formed in a manner so that as it reciprocated into the tapered portion of the tube, it will bend to conform to the shape of the tapered portion of the tip, providing a continuous contact at its front. This provides a highly efficient cutting action and, also, provides for increased blade life. As the wearing effect actually increases the contact surface, this increases the ability to cut thinner tissue.

It is therefore an object of the present invention to provide a novel surgical instrument having a flexible blade which is moved in a reciprocating manner.

A further object is to provide a surgical instrument having a tubular member with a tapered tip into which a flexible blade is moved, the tapered tip having an opening and the blade making a shearing cutting action as it moves past the opening.

Another object is to provide a surgical instrument having a tubular member with a tapered tip portion having a hole therein and a blade which changes its shape to conform to that of the tip portion as it is moved therein.

Other objects and advantages of the present invention will become more apparent upon reference to the following specification and annexed drawings in which:

FIG. 1 is an elevational view, partly in cross-section, showing the instrument;

FIG. 1A is a fragmentary cross view of the instrument tip, partly in cross-section, showing the blade in a deformed condition;

FIG. 2 is a front view of the instrument taken in cross-section along lines 2—2 of FIG. 1; and FIG. 3 is an enlarged view of the tip, taken in cross-section, and the blade.

Referring to the drawings, the surgical instrument 10 includes a housing 12 for a motor 14 which can be of either AC or DC type. The power connections to the motor are not shown but can be of any suitable type.

Motor 14 has a splined output shaft 16 which drives a mechanism for reciprocating the cutting blade. In a preferred embodiment of the invention, the reciprocating mechanism includes a cam 18 which is held within a narrowed down portion 20 extending from the housing 12. Cam 18 is cut with a track 22 in which rides a cam follower 24 which is attached to the inner wall of housing portion 20. The interior of cam 18 is splined to receive shaft 16.

A cutter drive shaft 34 is fastened to cam 18 by threads 33, over which a spring 30 is mounted over the end of shaft 34 and bears against a collar 32 on the shaft 34 which is adjacent the cam. At the opposite end of the shaft 34 from the collar 32 the flexible blade 38 is located. The blade is described in greater detail below.

The end of housing extension 20 is provided with a threaded portion 37 onto which a tube 40 is threaded. The fastening of the tube to extension 20 can be accomplished by any other suitable means, for example, soldering or welding. A fluid-tight seal is formed between tube 40 and housing extension 20 by having shaft 34 pass through an O-ring 44, or a similar sealing member, located in a seat in the housing extension 20. This seals the motor from the tube 40. Of course, any other suitable fluid sealing arrangement can be used, the particular type of sealing arrangement not being critical to the invention.

Tube 40 is hollow along its length and has a closed end, tapered tip portion 48 with an opening 50 cut therein. The opening 50 can be of any suitable shape depending upon the particular cutting action to be produced. That is, it can be circular, triangular, tear-shaped, elliptical, square, etc. As seen, the tapered tip portion 48 is of gradually decreasing diameter from that of the tube 40.

An outlet coupling fitting 54 is provided on the exterior of tube 40. Coupling 54 makes connection with a suitable source of reduced pressure, i.e., suction, 56 such that suction pressure can be applied along the length of tube 40 and be present at the opening 50. Similarly, if desired, a narrow diameter tube, of plastic or other suitable material, 60 can be located either inside or, preferably, on the outer surface of the tube 40 to supply air, water or other suitable fluid from a source (not shown). To accomplish this, the tube 40 can be formed with a trough 61 along its length to hold the tube 60 therein. The fluid supply tube 60 is not absolutely necessary.

As indicated previously, blade 38 is attached to the front end of the shaft 34. Blade 38 is of spring steel or other suitable metal material such as, for example, stainless steel, which has the properties of long life and capable of being sterilized. Blade 38 is formed from a flat metal piece which is cut to the shape desired and then bent so as to be able to fit within the tube 40. The blade is attached to a cylindrical spider 56 (FIG. 2) whose arms are fastened to the end of shaft 34. The blade is fastened to the spider by any suitable process, such as welding, brazing or soldering, and the spider is similarly connected to the shaft. The overall shape of the blade will conform to that of the spider, i.e., it will tend to have a cylindrical shape which is the same as that of the interior of tube 40.

As shown, blade 38 has a skirt portion 71 which is attached to the spider and then an arcuate shaped cutout 72 which is generally in the shape of a part of an ellipse. At the pointed end 73 of the arcuate cutout 72, the blade tapers upwardly at 74 in an arcuate manner and terminates in an edge 76 which can be curved or straight and is preferably sharpened.

By changing the shape of spider 56, other blade shapes can be obtained. For example, a rectangular configuration can be formed by pre-bending and/or pre-stressing the blade material to the desired shape and size and attaching it to a spider having flat walls.

The arcuate cutout 72 permits the blade to bend about the portion which has the least amount of material, i.e., in the arcuate space 72.

The instrument operates by moving blade 38 in a reciprocating manner with respect to the opening 50. This is accomplished by operating the motor 14 which will in turn rotate cam 18. As the cam rotates, the follower 24 rides in the track 18. The track is helical and has a return between its start and finish points. The follower 24 riding in track 22 will first move the cam 18 towards the right moving shaft 34 with it since cam 18 also slides with respect to splined shaft 16. During this movement, spring 30 is compressed. The dimensions of cam 18 and the layout of the track 22 are such that shaft 34 will be moved to the right a distance sufficient to move the edge 76 of the blade 38 from a point somewhat behind (to the left of) opening 50 to a point where the blade edge 76 has passed completely under the opening 50 and lies somewhat beyond its forward edge. At this point in time, the cam causes the shaft to reverse direction and moves the blade from the right to left uncovering the opening 50. The force of the compressed spring 30 will assist in moving shaft 34 and blade 38 back to the left. Since the motor 12d turns continuously, a reciprocating action of the shaft 34 and blade 38 is produced. That is, the blade travels back and forth with respect to opening 50.

As the shaft 34 is moved to the right, at which time the blade leaves the larger diameter portion of the tube 40, the edge 76 of the blade begins to encounter the tube's tapered tip 48. At this point in time, the engagement of the outer surface of the blade 38 with the inner surface of the wall of tip 48 causes the blade to curve inwardly to be of a lesser diameter. At the same time the upper part of the blade will encounter force as it moves against the inner wall of tip 48. This causes the blade 76 to bend downwardly at the portion bridging the cutout 72. Thus, there is not only a narrowing of the overall diameter of the blade as it moves further into the tip 48 but at the same time there is a bending movement. The action is such that the blade sweeps across the opening 50 in a plane generally parallel to the plane of the opening.

Depending upon the sizing of the blade with respect to the tube 40 and its tip 48, the edge 76 of the blade can be in contact at all times with the inner surface of tip 48 as it is sweeping across the opening 50. Alternative to this, the force for bending the blade downwardly can be obtained at the corners of the blade edge 76 so that the portion of the blade which passes under the opening 50 does not have to make an engaging contact with the tube 40. This improves its life. If desired, some sort of a bearing can be placed at the points 73, for example, the blade could be dimpled outwardly.

At the same time that the reciprocating action is taking place, suction pressure is applied from the source 55 and is present at opening 50 through the spider 56. This will draw tissue from the operating field in through the opening 50. The tissue which extends into the opening 50 is cut by each pass of the blade 38 across the opening 50. The action is of a shearing nature. If desired, the wall of tip 48 surrounding the opening 50 can be sharpened. When desired, a fluid from tube 60 can be supplied to irrigate the operating field.

What is claimed is:

1. A surgical instrument comprising:
   a hollow tubular member having a tip portion which tapers to a smaller diameter than the major part of the member, said tapered tip having an opening formed therein,
   a shaft within said tubular member,
   means for reciprocating said shaft toward and away from said tapered tip of said tubular member,
   a blade mounted on said shaft and having a first portion adapted to move within the tapered tip of said tubular member, said blade formed to deform by engaging the tubular member and to conform to the tapered shape of the tip as the blade is moved further into said tip so that the blade makes a shearing cut of material in the tip opening in cooperation with the wall of the tubular member surrounding the opening as the blade sweeps across the opening.

2. A surgical instrument as in claim 1 wherein said blade is formed of a piece of sheet material which is bent to conform to the shape of the tubular member.

3. A surgical instrument as in claim 1 wherein said first portion of said blade has a sharpened edge to sever material entering said opening of the tubular member tapered tip portion by a shearing action between said sharpened edge and the wall of the tubular member surrounding said opening.

4. A surgical instrument as in claim 1 wherein said front portion of said blade includes a sharpened edge.

5. A surgical instrument as in claim 1 wherein said blade is formed as a generally arcuate surface, a portion of said surface being removed to provide a hinge area about which the blade can bend when force is applied thereto by contact with the inner wall of the tip.

6. A surgical instrument as in claim 5 wherein the cutout portion of the blade surface is generally arcuate and the blade surface tapers from the end of the cutout portion toward the tip of the blade.

7. A surgical instrument as in claim 1 wherein said means for reciprocating said shaft comprises a cam and cam follower, motor means for rotating said cam, and said shaft being attached to said cam.

8. A surgical instrument as in claim 1 wherein the blade is formed to decrease its diameter as it is moved further into the tapered tip.

9. A surgical instrument as in claim 8 wherein the blade has a portion which is also found to deform inwardly of the tip as the blade is moved further into the tip.

* * * * *